US00PP12858P2

(12) United States Plant Patent
Glick

(10) Patent No.: US PP12,858 P2
(45) Date of Patent: Aug. 13, 2002

(54) EUPHORBIA PLANT NAMED 'JESSIE'

(75) Inventor: Barry Glick, Renick, WV (US)

(73) Assignee: Sunshine Farms & Gardens, Renick, WV (US)

( * ) Notice: Subject to any disclaimer, the term of this patent is extended or adjusted under 35 U.S.C. 154(b) by 14 days.

(21) Appl. No.: 09/761,474

(22) Filed: Jan. 18, 2001

(51) Int. Cl.[7] ..... A01H 5/00

(52) U.S. Cl. ..... Plt./302

(58) Field of Search ..... Plt./302

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Euphorbia plant named 'Jessie', characterized by its freely flowering habit and bright yellow floral bracts and whorl leaves with distinct orange margins.

1 Drawing Sheet

BACKGROUND OF THE INVENTION

The present invention relates to a new and distinct cultivar of Euphorbia, botanically known as *Euphorbia griffithii* ×*Euphorbia epithymoides* and hereinafter referred to by the cultivar name Jessie.

The new Euphorbia is a product of a planned breeding program conducted by the Inventor in Renick, W. Va. The objective of the breeding program is to create new Euphorbia cultivars with unique and desirable flower colors.

The new Euphorbia originated from a cross made by the Inventor in Renick, W. Va., of the *Euphorbia griffithii* cultivar Fireglow, not patented, as the female, or seed, parent with an unidentified selection of *Euphorbia ephithymoides,* not patented, as the male, or pollen, parent. The cultivar Jessie was discovered and selected by the Inventor as a flowering plant within the progeny of the stated cross in a controlled environment in Renick, W. Va., in June, 1998.

Compared to plants of the female parent, the cultivar Fireglow, plants of the new Euphorbia are more erect. Floral bracts and whorl leaves of the new Euphorbia are bright yellow in color whereas floral bracts and whorl leaves of the cultivar Fireglow are reddish orange in color. In addition, plants of the new Euphorbia have green stems, peduncles and pedicels whereas plants of the cultivar Fireglow have red stems, peduncles and pedicels.

Compared to plants of the flowered male parent, plants of the new Euphorbia are taller and have narrower leaves. Floral bracts and whorl leaves of the new Euphorbia are bright yellow in color whereas floral bracts and whorl leaves of the male parent are yellowish green.

Asexual reproduction of the new Euphorbia by terminal cuttings taken in a controlled environment in Renick, W. Va., has shown that the unique features of this new Euphorbia are stable and reproduced true to type in successive generations.

SUMMARY OF THE INVENTION

The cultivar Jessie has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Jessie'. These characteristics in combination distinguish 'Jessie' as a new and distinct cultivar:

1. Freely flowering habit.
2. Bright yellow floral bracts and whorl leaves with distinct orange margins.

BRIEF DESCRIPTION OF THE PHOTOGRAPH

The accompanying colored photograph illustrates the overall appearance of the new Euphorbia, showing the colors as true as it is reasonably possible to obtain in colored reproductions of this type. Colors in the photograph may differ slightly from the color values cited in the detailed botanical description which accurately describe the colors of the new Euphorbia. The photograph comprises a close-up view of typical flowers of 'Jessie'.

DETAILED BOTANICAL DESCRIPTION

The following observations, measurements and values describe plants grown in Renick, W. Va., during June and July under outdoor field conditions which closely approximate commercial production. Day temperatures during this time ranged from 21 to 29° C. and night temperatures ranged from 9 to 14° C. Plants used for the description were about 12 months old. In the description, color references are made to The Royal Horticultural Society Colour Chart except where general terms of ordinary dictionary significance are used.

Botanical classification: *Euphorbia griffithii* ×*Euphorbia ephithymoides* cultivar Jessie.

Parentage:

*Female or seed parent.*—*Euphorbia griffithii* cultivar Fireglow, not patented.

*Male or pollen parent.*—Unidentified selection of *Euphorbia ephithymoides*, not patented.

Propagation:

*Type.*—By terminal cuttings.

*Time to initiate roots.*—About 10 to 14 days at temperatures of 21° C.

*Time to develop roots.*—About 14 to 28 days at temperatures of 21° C.

*Root description.*—Thick and well-branched.

Plant description:

*Plant form and frowth habit.*—Upright, columnar plant habit; perennial subshrub. Rapid growth rate.

*Branching habit.*—Freely branching, usually about five lateral branches develop after removal of terminal apex.

*Plant height, soil level to top of flowers.*—About 1.4 meters.

*Plant diameter, area of spread.*—About 60 cm.

*Lateral branch description.*—Length: About 18 cm. Diameter: About 5 mm. Internode length (mid-plant): About 1.9 cm. Strength: Strong, flexible. Texture: Pubescence at nodes. Color: 144A to 144B with anthocyanin, close to 59A, on upper surfaces.

Foliage description:

*Stem leaves.*—Arrangement: Alternate, single; symmetrical; sessile. Quantity: About 18 to 20 leaves per lateral branch. Length, basal leaves: About 13.5 cm. Width, basal leaves: About 3.5 cm. Shape: Elongated oblong. Apex: Acute. Base: Attenuate to slightly cordate. Margin: Entire. Texture: Glabrous; smooth; flexible; leathery. Color: Young foliage, upper surface: Close to 144A. Young foliage, lower surface: Close to 147C. Mature foliage, upper surface: More green than 146A to close to 147A; venation, 155D. Mature foliage, lower surface: Close to 147B; venation, 147D to 155D.

*Whorl leaves.*—Quantity/arrangement: About five in a whorl at the base of primary cymes; about three at the base of secondary cymes; symmetrical; sessile. Length: About 5.3 cm. Width: About 2.1 cm. Shape: Narrowly ovate to elongated oblong. Apex: Acute. Base: Slightly cordate. Margin: Entire. Texture: Glabrous; smooth; flexible; leathery. Color: Young foliage, upper surface: Close to 9A with green, close to 144A to 146A, undertones; distinct orange, close to 28A, margin. Young foliage, lower surface: Close to 9C with faint greenish, close to 146A, undertones. Mature foliage, upper surface: Close to 9A to 12A with green, close to 146A to 147A, undertones; distinct orange, close to 28A, margin; venation, 155D. Mature foliage, lower surface: 147B; venation, 147D to 155D.

Flower description:

*Natural flowering season.*—Late June through early to mid-July in West Virginia.

*Flower arrangement.*—Flowers arranged in umbel-like compound cymes; primary cymes, 5-merous and secondary cymes, 3-merous. Very freely flowering with about 400 flowers per plant. Flowers upright; persistent; and not fragrant.

*Inflorescence height.*—About 4.4 cm.

*Inflorescence diameter.*—About 7.8 cm.

*Flower diameter.*—About 1.75 cm by 8 mm.

*Flower depth.*—About 8 mm.

*Flower longevity.*—About three to four weeks.

*Floral bracts.*—Quantity/arrangement: Two or three, opposite or in a whorl, subtending cyathium. Length: About 8.5 mm. Width: About 8 mm. Shape: Broadly ovate. Apex: Acute. Base: Attenuate. Margin: Entire. Texture: Glabrous; smooth. Color: When opening and mature, upper surface: Bright yellow, close to 9A to 15A, with distinct orange, close to 28A, margin. When opening and mature, lower surface: Bright yellow, close to 9B to 9C, with distinct orange, close to 28A, margin.

*Cyathia.*—Arrangement: Involucre of cyathium cup-shaped; 4-lipped; upright. About three petaloid appendages subtending the cyathia, 2 mm by 1 mm, bright yellow, close to 9A. Height: About 3 mm. Diameter: About 4.5 mm. Color: Immature, 154C; mature, 21A.

*Peduncles.*—Length: About 2.8 cm. Diameter: About 1.25 mm. Angle: About 45 to 55° from vertical. Strength: Strong, flexible. Texture: Smooth. Color: 144B.

*Pedicels.*—Length: About 5 mm. Diameter: Less than 1 mm. Angle: About 45° from vertical. Strength: Strong, flexible. Texture: Smooth. Color: 144B.

*Reproductive organs.*—Androecium: Stamen number: About 2 to 4. Anther shape: Bi-lobed. Anther length: Less than 1 mm. Anther color: Close to 21A. Amount of pollen: None observed. Gynoecium: Pistil number: One. Pistil shape: Tri-parted. Pistil length: About 4 mm. Style length: About 2.1 mm. Style color: 154A to 154B. Stigma shape: Bi-lobed. Stigma color: 59A. Ovary diameter: About 2 mm. Ovary color: 154A to 154B.

*Seed.*—Seed production has not been observed.

Disease resistance: Plants of the new Euphorbia have not been observed to be resistant to pathogens common to Euphorbia.

Temperature tolerance: Plants of the new Euphorbia are tolerant to temperatures as low as −32° C. and as high as 32° C.

It is claimed:

1. A new and distinct Euphorbia plant named 'Jessie', as illustrated and described.

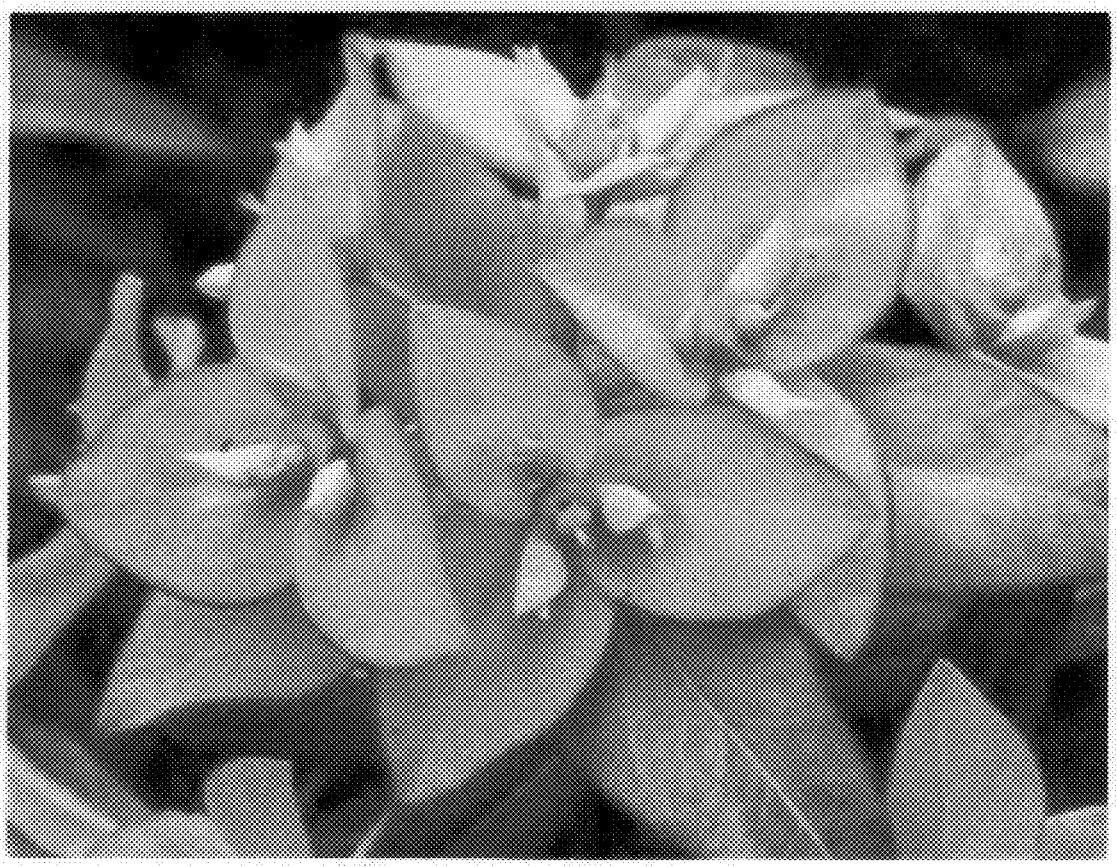

* * * * *